United States Patent [19]
Flomenblit et al.

[11] Patent Number: 5,964,770
[45] Date of Patent: Oct. 12, 1999

[54] HIGH STRENGTH MEDICAL DEVICES OF SHAPE MEMORY ALLOY

[75] Inventors: Josef Flomenblit; Nathaly Budigina, both of Holon; Jacob Richter, Ramat Hasharon, all of Israel

[73] Assignee: Litana Ltd., Holon, Israel

[21] Appl. No.: 08/940,525

[22] Filed: Sep. 30, 1997

[51] Int. Cl.$^6$ .................................................. A61B 17/56
[52] U.S. Cl. ........................ 606/78; 606/76; 606/108; 606/192; 606/198; 606/200; 604/281
[58] Field of Search ................... 606/76, 78, 108, 606/192, 198, 200; 604/281

[56] References Cited

U.S. PATENT DOCUMENTS

| | | | |
|---|---|---|---|
| 4,485,816 | 12/1984 | Krumme | 606/78 |
| 4,665,906 | 5/1987 | Jervis | 606/78 |
| 5,201,901 | 4/1993 | Harada et al. | 606/198 |
| 5,545,210 | 8/1996 | Hess et al. | 623/1 |
| 5,562,641 | 10/1996 | Flomenblit et al. | 604/281 |

*Primary Examiner*—Michael Buiz
*Assistant Examiner*—(Jackie) Tan-Uyen T. Ho
*Attorney, Agent, or Firm*—Gary M. Nath; Nath & Associates; Harold L. Novick

[57] ABSTRACT

A medical device such as a stent, surgical staple, bone anchoring device or bone fixation device, intended to be deployed within the body, composes a shape memory alloy (SMA) portion with an austenitic and unaustenitic state with different memorized configurations in each of these states. The SMA which is initially in an initial configuration in which it can be placed into position within the body, can be mechanically deformed into an operational configuration in which it remains deployed within the body.

12 Claims, 8 Drawing Sheets

HIGH STRENGTH MEDICAL DEVICES OF SHAPE MEMORY ALLOY

FIELD OF THE INVENTION

The invention relates to implantable medical devices, and more particularly, to implantable medical devices made of or have at least a portion made of a shape memory alloy (SMA), which are positioned in the body while being in an initial configuration, another deformed to a second, operational configuration (the configuration assumed by the device once deployed in the body).

BACKGROUND OF THE INVENTION AND PRIOR ART

Implantable medical devices, such as stents, heart valves, bone plates, staples, intrauterine contraceptive devices and the like must meet many requirements to be useful and safe for their intended purpose. For example, they must be chemically and biologically inert to living tissue and to be able to stay in position over extended periods of time. Furthermore, devices of the kind mentioned above must have the ability to expand from a contracted state, which facilitates insertion into body conduits or cavity, to a useful expanded diameter. This expansion is either accomplished by a forced expansion, such as in the case of certain kinds of stent by the action of a balloon-ended catheter, or by self-expansion such as by shape-memory effects.

There are many alloys which display a shape memory effect (SME), known generically as shape memory alloys (SMAs). A widely used metal alloy, particularly for metal applications, is the nickel-titanium alloy, known as "nitinol". Under certain conditions, SMAs can be highly elastic such that they are able to undergo extensive deformation and yet return to their original shape. Furthermore, SMAs possess shape memory properties such that they can "remember" a specific shape imposed during a particular heat treatment and can return to that imposed shape under certain conditions.

The shape memory effect of SMAs results from metallurgical phase transformations. Certain SMAs are characterized by a transition temperature or transition temperature range, above which the predominant metallurgical phase is termed "austenite" and below which the predominant metallurgical phase is termed "martensite". The transformation from austenite (or austenitic state) to martensite (or martensitic state) is termed "martensitic transformation"; the reverse transformation from martensite to austenite is termed as "austenitic transformation". The transformations in fact occur over a range of temperatures and are commonly discussed with reference to $M_s$ and $M_f$, the start and finish temperatures of the martensitic transformation, respectively, and $A_s$ and $A_f$, the start and finish temperatures of the austenitic transformation, respectively. Transformation between these two phases is reversible such that the alloys may be treated to assume different shapes or configurations in the two phases and can reversibly switch between one shape to another when transformed from one phase to the other. Occasionally, SMAs display an intermediate phase, between the austenitic and martensitic states, known as the "R phase". Transformation from austenite to the R phase can also be temperature induced, occur at a temperature referred to as "$T_R$". The R phase alone does not impart a significant SME (its recoverable strain does not exceed 1%), in contrast to the austenite and martensite states, but rather is a phase strongly affecting the mechanical properties of the alloy and the SME.

Implantable medical devices made of SMA have been known in the art. See for example U.S. Pat. Nos. 3,786,806, 4,485,816 and 5,037,427. U.S. Pat. No. 5,242,451 discloses a stent employing a unidirectional SME to conform into an operational shape, from an original basic shape of a smaller diameter. In U.S. Pat. No. 5,562,641, a two-way SME is employed such that the austenitic transformation temperature is above body temperature and the martensitic transformation temperature is below body temperature, whereby the device retains its last conditioned state (e.g. austenite or martensite) at body temperature. U.S. Pat. No. 5,545,210 discloses a stent which is mechanically deformable while in a martensitic state into an operational configuration assumed by it when it is deployed in a tubular organ. The stent of U.S. Pat. No. 5,545,210 exhibits, in its operational configuration, a strain which is on the horizontal plateau of the stress-strain curve of the SMA. U.S. Pat. No. 5,624,508 disclosed a method for the manufacture of shape memory alloy (SMA) device with defined transformation temperature.

The use of stress-induced martensite principle, rather than temperature-induced martensite, has likewise been employed in SMA-based medical devices, e.g. in U.S. Pat. No. 4,665,906. In such devices, austenitic nitinol is deformed to form stress-induced martensite and held in its deformed configuration and martensitic state by a restraining member. The device is introduced into the body in the deformed configuration, where it is released from the restraining member to return to its austenitic state and configuration without any temperature change.

GENERAL DESCRIPTION OF THE INVENTION

The present invention relates to implantable medical devices such as stents, heart valves, bone plates, surgical clips or staples, tooth implants, bone fracture healing device, catheters, interuterine contraceptive devices, and the like.

In the following, the term "shape memory device" will be used to denote a device which is made entirely or having at least a functional portion made of a shape memory alloy (SMA). The term "functional portion" means to denote a portion of the medical device which can change its configuration to perform a certain function within the body (e.g. anchoring, applying force on surrounding tissue, etc.). The shape memory device of the invention utilizes some of the shape memory properties of the SMA for its function. The term "configuration" should be understood as meaning either one or more of the shape, diameter, elasticity, mechanical properties, or any other mechanical and geometrical property of the SMA. The configuration is in fact a combination of all such properties.

The medical device of the invention has at least a functional portion comprising an SMA of the two-way shape memory type; namely, an SMA having two different "memorized" configurations, including one assumed by it in its austenitic state (to be referred to herein at times as the "austenitic configuration") and the other assumed by it in its martensitic state (to be referred to herein at times as the "martensitic configuration"). Each of these different configurations is also typically characterized by a different geometrical shape, which will be referred to herein at times respectively as the "austenitic shape" and the "martensitic shape".

The invention, by some of its embodiments, employs a mechanical deformation in martensite, having some properties resembling those of a plastic deformation, for deployment of the device within the body and to assume an operational shape, with a deformation strain which is less than the maximal recoverable strain (the term "recoverable strain" is to denote that by an increase of temperature above the austenitic temperature, the strain is released and the SMA conforms to its austenitic configuration). By some embodiments, the maximal recoverable strain can be improved and the fatigue resistance can be increased by having an intermediate R phase.

The device of the invention in accordance with some embodiments has an austenitic configuration such that the process of deformation from the martensitic state to the austenitic state is in a direction opposite to that of the process of mechanical deformation from the initial configuration to the operational configuration of the SMA. In other embodiments, the deformation of the austenitic transformation is in the same direction of the mechanical deformation.

By another embodiment of the invention use is made of the SMAs ability to undergo a strain-induced or a stress-induced mechanical transformation ("mechanically-induced martensitic transformation—"MIMT") to yield a mechanically-induced martensitic state ("MIMS"). Specifically, this property, combined with the general mechanical properties of the SMA, further combined with the mechanical properties of a plastic element associated with the SMA, is used to advantage of preparing a composite clement, having on the one hand, "simulated" plastic deformation properties (the are "simulated" because there results from the combined properties of two different materials which together in a certain range of their properties, and which plays a role in the mechanical deformation display together with plastic deformation properties) with however very strong mechanical strength in an operational state, without practically any recoil.

The present invention provides, a medical device for deployment in a body of an individual, comprising a shape memory alloy (SMA) portion having an austenitic and a martensitic state, with different memorized configurations in each of these states, and being transformable between the martensitic state to the austenitic state by an austenitic transformation occurring at an austenitic transformation temperature, and from the austenitic state to the martensitic state by a martensitic transformation occurring at a martensitic transformation temperature, the SMA having an initial configuration which is either a memorized austenitic configuration of the SMA or a martensitic configuration assumed by the SMA portion by a mechanical deformation; the SMA portion being mechanically deformable from the initial configuration into an operational configuration to be assumed by it when deployed within the body; the SMA portion in the operational configuration is either in a martensitic state and having a memorized austenitic configuration to which it transforms when heated to a temperature, equal or above the austenitic transformation temperature, which is above body temperature, or is in an austenitic state, to which it transformed during the mechanical deformation.

The medical device is positioned into its intended place within the body when in its initial configuration and this converted to the operational configuration in which it remains deployed within the body.

The $A_f$ temperature (as well $A_s$, $M_s$ and $M_f$) can change as a result of a mechanical deformation. $A_f$ which has changed as a result of a mechanical deformation will be identified by a "'" indication, i.e. "$A_f'$".

By one embodiment of the invention, the SMA portion has in its operational configuration, an $A_f$ which is higher than physiological body temperature, $T_B$, and an $M_s$ which is lower than $T_B$; the SMA portion being deformable, while retaining its martensitic state into said operational configuration; upon heating of the SMA portion to a temperature above $A_f'$, it undergoes an austenitic transformation into the austenitic configuration, which is a different configuration than said operational configuration, with the SMA remaining in the austenitic configuration after the SMA's temperature returns back to $T_B$. The austenitic configuration may be such so that the transformation from the operational configuration to the austenitic configuration, when the device is heated to a temperature above $A_f$, goes in a direction opposite to the forced deformation from the initial to the deployment configuration. In accordance with another embodiment, the transformation from the operational configuration to the austenitic configuration is in the same direction to that of said forced configuration.

In accordance with one embodiment of the invention, the SMA has an undeformed martensitic configuration, namely a configuration assumed by it after undergoing a heat-induced martensitic transformation, which is about the same as the operational configuration. In such an SMA, internal stress sources will function to stabilize the SMA portion in the operational configuration.

According to another embodiment, the device has an intermediate state R, between the martensitic and the austenitic states, and having a transformation temperature from the austenitic state to the R state $T_R$, which is higher than $M_s$ and being close to $T_B$, such that at body temperature, the SMA portion is entirely or partially in the R state. For example, $T_R$, may be about 35° C. and $M_s$ about 32° C.

In accordance with an embodiment of the invention the deformation of the SMA from the initial shape to the deployment shape is with a strain within a range of $\epsilon_1$–$\epsilon_2$, with $\epsilon_1$ being a strain level at an end of a horizontal plateau of a stress-strain curve of the SMA, and $\epsilon_2$ is an upper limit of deformation where recoverable by a shape memory effect (namely the upper limit of the deformation in which the device can still undergo an austenitic transformation into the austenitic configuration). Typically, the SMA portion is made to assume its initial shape by an elastic deformation while in the martensitic state.

In accordance with a further embodiment of the invention, the forced deformation of the SMA portion causes an increase in the austenitic transformation temperature from initial start and finish transformation temperatures of the austenitic transformations, $A_s$ and $A_f$, respectively, which are below $T_B$, to austenitic start and finish transformations in the operational configuration, $A_s'$ and $A_f'$, respectively, higher than $T_B$.

The SMA portion in a device according to the latter embodiment, may be made to have an R phase with a $T_R$ close to $T_B$, and may then be mechanically deformed such that at least one segment of the SMA portion remains in the R phase and at least one other segment is deformed with a strain at the range of $\epsilon_1$–$\epsilon_2$. Thus, in its operational configuration, the SMA portion will have at least one segment (that which is in the R phase) which is relatively soft and flexible, and at least one segment (that deformed with a strain within the range of $\epsilon_1$–$\epsilon_2$) which has a high mechanical strength.

According to another embodiment of the invention there is provided a medical device for deployment in a body of an individual, comprising:

a first component and a second component associated with one another, such that a deforming mechanical force cause both to deform together; the first component comprising an SMA having an initial configuration in which the SMA is in a mechanically induced martensitic state (MIMS) resulting from a strain-induced or stress-induced martensitic transformation; the second component having mechanical properties such that it resists deformation at a stress, $\sigma_2$, which is larger than stress generated by the SMA when released from said MIMS to the austenitic stress, $\sigma_1$, thereby restraining said SMA in said initial state; the SMA together with the second component are mechanically deformable from said initial configuration to an operational configuration, this deformation causing the SMA to transform from said MIMS to the austenitic state; the plastic element yielding a reactive stress, $\sigma_2$, which is less than the resistive stress, $\sigma_3$ of the deformation of the SMA from the operational configuration to said initial configuration, whereby the device is retained in said operational configuration.

The second component in a device in accordance with the above embodiment, may have plastic mechanical properties, i.e. a low recoil. The SMA portion in such device provides resistance against the surrounding tissue, where the device has been deployed, which may be adjusted between 0 up to a level depending on the difference between $\sigma_4$ (the stress during relaxation of the second component) and $\sigma_3$. The second component may also be elastic, i.e. have a high recoil, up to about 100%, with the SMA portion having an R phase with a $T_R$ transformation temperature below $T_B$, whereby cooling of the SMA to $T_R$ or below causing a very sharp drop of the SMA's elastic modulus giving rise to a decrease in the stiffness of the SMA portion, and the second component can then deform the SMA portion up to at least said initial configuration and maintain in this configuration, such that it can be removed or repositioned.

The second component may be made of a variety of materials including, for example, rubber, silicone, metal with different mechanical properties to the SMA, SMAs with different properties, polymeric plastic material, etc.

A device in accordance with the above embodiment, combines the properties of the SMA and those of the second component so as to yield properties which (luring the mechanical deformation, simulate an essentially perfect plastic deformation; but if the SMA portion has an R phase and the SMA portion is transformed to said R phase by cooling temperature to $T_R$, the device displays elastic properties. (Such combined properties, will be referred to herein as "simulated plastic deformation" or "simulated elastic deformation" properties, respectively).

The invention will now be further illustrated in the following non-limiting specific embodiment with occasional reference to the annexed drawings:

DETAILED DESCRIPTION OF THE INVENTION

Figure 1:
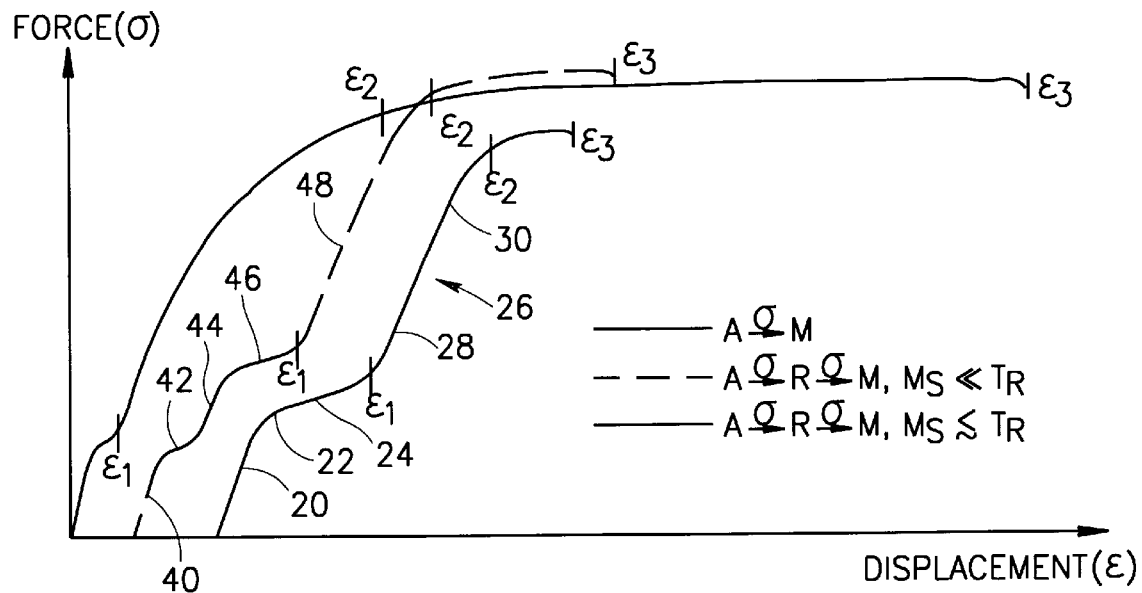
FIG. 1 shows a stress-strain curve for three different shape memory alloys: a standard alloy displaying an austenitic to martensitic transformation (curve 1); an alloy displaying an austenitic to a martensitic transformation, with an intermediate R state, with $M_S$ being very much lower than $T_R$ (curve 2); and an alloy with an intermediate R state, but with $M_s$ smaller than but very close to $T_R$.

The invention relates to a medical device having an SMA portion which is mechanically deformed from an initial configuration in which it is inserted into the body, to an operational configuration, which it assumes when deployed in the body. The deformation is not elastic, since after the external deforming force is unloaded, the SMA portion remains in the deformed state. However, the deformation is also not plastic, since, depending on the type of embodiment, the device can recover its austenitic configuration by austenitic transformation when heated to a temperature above $A_f$, or alternatively, the SMA portion after the forced deformation is in the austenitic state (in the last embodiment described above).

The medical device of the invention may be any one of those mentioned above. A medical device of the invention being a stent is a preferred embodiment of the invention, although the invention should definitely not be considered as being limited to this embodiment only. Occasionally, in the following text, reference will be made specifically to a medical device being a stent, this being meant for illustration purposes only.

The SMA used in accordance with the invention may be any of a variety of such alloys known in the art, nitinol being preferred. Nitinol, which is an alloy comprising primarily nickel and titanium, may also, at times, comprise other metals, typically in trace amounts, including copper (Cu), iron (Fe), chromium (Cr), vanadium (V). The alloy comprises about 50 atomic % of both nickel (Ni) and titanium (Ti) with occasionally some of the nickel or the titanium being replaced by one of the abovementioned other metals, e.g. in a concentration range of 0.3–2 atomic %.

The medical device is inserted into the body in an initial configuration, adapted for such insertion, and then is deformed by a mechanical deformation into the operational configuration, in which it remains deployed within the body. For example, in the case of a stent, the initial configuration may be a configuration wherein the stent is coiled around the end of a balloon catheter; the balloon catheter is then used to mechanically deform and expand the stent into its operational configuration, where it has a wider diameter supporting the wall of a tubular organ. The device of the invention may be made entirely of SMA, in which case said SMA portion will in fact constitute the entire device. Alternatively, in some cases the medical device of the invention may have only a portion, a large or a small portion, which is made of an SMA possessing the two-way SME properties.

A medical device which is mechanically deformable from an initial state into an operational state, should ideally possess the following characteristics:

(a) after the forced mechanical deformation, it should have the mechanical strength so as to resist any reactive forces from the surrounding tissue, so that it will not collapse;

(b) The device should be resistant to fatigue, particularly in the case of a varying reactive force, e.g. those applied on a stent by the walls of an artery. Fatigue resistance means in essence resistance against breaks;

(c) It should have a maximal recoverable strain to provide a wide spectrum of design of the SMA portion. This means in essence, that the SMA portion can undergo deformation with a considerable strain, e.g. about 10%, with strain recovery after heating (SME realization).

(d) The device should have a minimal spring back (recoil). The recoil is in fact an instantaneous, elastic deformation in a direction opposite to the forced deformation, which occurs immediately after force unloading (i.e. after stopping the application of force). Such recoil may cause disengagement between the SMA portion and the surrounding tissue, e.g. between a stent and the surrounding walls of an artery, and or as a result impairment in function and unwanted dislocation.

The present invention achieves the above objectives by employing an SMA of the two-way shape memory type, and particularly by making a novel use of the SMA's, state-dependent mechanical properties.

In the following, the letters A, M and R will be used to denote the austenitic state, the martensitic state and the R phase, respectively. The conversion from one state to another will be used by indicating the letter of the starting phase or state connected by a hyphen to the letter pertaining to the resulting state or phase (for example, A–M denotes transformation from austenite to martensite).

Reference is made first to FIG. 1 showing the strain-stress relationships of three different SMA alloys, represented by curves 1, 2 and 3. It should be noted that the point of intercept of each of these curves with the horizontal axis is arbitrary and the different curves are shifted along this axis for the sake of clear presentation. Curve 1 shows the stress-strain relationships of an SMA which undergoes a deformation-induced A–M transformation. In the first vertical part of the curve 20 the SMA is A until the bend 22 when the SMA enters into the horizontal plateau of strain-stress curve in which it converts from A to M. In the horizontal plateau 24 the SMA is relatively soft, and thus a small stress yields a relatively large deformation. In U.S. Pat. No. 5,545,210 (Hess et al.) it is proposed to use a stent which when permanently positioned in a tubular organ, exhibits a strain which is on the horizontal plateau 24, i.e. a strain below $\epsilon_1$. It may be appreciated that such a stent will exhibit a relatively small mechanical strength. The present invention is based on the realization that the transformation should preferably be to a strain within region 26 of the curve, mainly between $\epsilon_1$ and $\epsilon_2$. $\epsilon_2$ is the maximal recoverable strain, namely where the SMA still retains its memory properties. At a strain above $\epsilon_2$ the SMA loses its shape memory properties and cannot recover all strain during M–A transformation. (In fact, it should be noted that the austenitic transformation temperature is also dependent on the degree of deformation, i.e. increases with increase in deformation).

It should be noted, that the SMA, as any alloy, has a maximal deformation which causes it to break, $\epsilon_B$. The extent of strain difference between a certain deformed configuration and the maximal strain $\epsilon_B$, is a measure of the fatigue resistance of the SMA: a large difference meaning a large fatigue resistance, and vice versa.

Segment 26 of the curve has in fact two portions, a lower portion 28, where the SMA has some elasticity, and an upper portion where the SMA is "plastic" (the SMA in this portion is not actually plastic and the deformation, even of this portion is not a real plastic deformation, since the martensite has a "memorized" austenitic configuration which is recoverable by a heat-induced transformation). It is preferred in accordance with the invention that the deformation will he to a strain where the SMA displays plastic-like properties (segment 30) on the one hand and large mechanical strength on the other hand.

$\epsilon_2$ in an SMA portion in a device of the invention is typically 8–12% (measured from the point of intersection of the curve with the horizontal axis).

The deformation of the medical device to a strain within the range of $\epsilon_1$–$\epsilon_2$ where it displays much higher mechanical strength than conventional mechanically deformed medical devices, particularly stents. (Hitherto, mechanically deformable medical devices were deployed by deformation to a strain in the range of the horizontal plateau, as noted above). This increase strength allows the medical device of the invention to better resist reaction forces exerted on the device by surrounding tissues or organs. While not wishing to be bound by theory, it is believed that strengthening of the device by deforming it into the region $\epsilon_1$–$\epsilon_2$ occurs by the interaction between dislocations and martensite plates of different variants.

Figure 2:
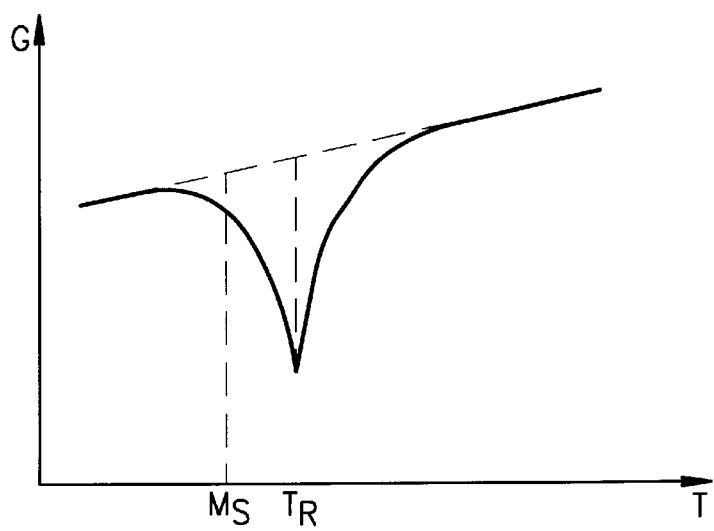
FIG. 2 shows the shift modulus as a function of the temperature, of an alloy of the kind of curve 3 in FIG. 1.

Curve 2 in FIG. 1, relates to an SMA having an intermediate R phase between A and M and thus undergoes a mechanically induced transformation first from A to R (A–R) and then from R to M (R–M). The A–R transformation can also be temperature induced, at a transformation temperature $T_R$. $T_R$, is made to be larger than $M_s$ and in the specific case of the SMA of curve 2, is considerably larger. Against this, in curve 3 which relates to an alloy which also undergoes an A–R–M deformation induced transformation, the $M_s$ is only slightly below, e.g. 1° C.–10° C. below, $T_R$. One of the characteristics of the R phase is a low shift module at a temperature $T_R$, as represented in FIG. 2. In the case of the present invention $T_R$ is made to be about the same as the body temperature, i.e. about 37° C., which is the temperature in which the mechanical deformation is being carried out. $T_R$ of the alloy, is larger than $M_s$, as aforesaid, but should be smaller than As, which is above body temperature. This means that under mechanical deformation stresses, the SMA portion of the device transforms from A to R and then from R to martensite. This A–R–M transformation has more stages than the previous case of the A–M transformation, including a first stage 40, where the SMA is A, a horizontal stage 42 where the A–R transformation occurs, a stage 44 where the SMA portion is the R, a horizontal stage 46 where the R–M transformation occurs and then the stage of reversible martensitic transformation (interaction of different martensitic variants) 48 which extends between strain rates $\epsilon_1$ and $\epsilon_2$ ($\epsilon_1$ and $\epsilon_2$ in curve 2 may have different values than $\epsilon_1$ and $\epsilon_2$ in curve 1). The same applies for the values $\epsilon_1$ and $\epsilon_2$ of curve 3). This multi-phase deformation curve allows an increase in total recoverable strain as compared to a one phase transformation.

Small differences between $T_R$ and $M_s$ gives rise to an R–M transformation under favorable conditions of decreased elastic modules (see again FIG. 2). An alloy where $M_s$ and $T_R$ are very close to one another, is that which yields curve 3 in FIG. 1. The R and M in fact "blend" with one another to yield a relatively wide range of $\epsilon_1$–$\epsilon_2$, in which the "plastic" deformation occurs, yielding a strong, deformation resistance configuration in martensite.

In addition to the larger recoverable strain of an SMA with an R state, the decrease in the elastic shift modulus increases the strain where break may occur, $\epsilon_3$, thus yielding an increase in the fatigue resistance of the SMA. This is particularly apparent in the case of curve 3 where $M_s$ is close to $T_R$.

In addition, the existence of an R phase decreases the elastic spring back (recoil) of the SMA. For example, in the case of a wire intended to be used as a force element of a bone fracture healing device, the existence of an R phase provides a recoil of 12% and a recoverable strain of 11%; direct A–M deformation yields recoil of about 25%–28% and about 7.5% recoverable strain.

Another property which is utilized in accordance with the invention is the increase in the austenitic transformation temperatures, which was already pointed out above. The SMA can be designed to have an initial austenitic transformation temperature ($A_s$ and $A_f$) which is lower than body temperature ($T_B$), with this transformation temperature increasing after the mechanical deformation to a temperature $A_s'$ and $A_f'$, which is above $T_B$. The austenitic transformation, namely the temperature induced change in configuration between M to A, can be in the same or in the opposite direction of the mechanical deformation. Where the austenitic transformation occurs in the opposite direction of the mechanical deformation, the device may be inserted into the body in the austenitic state and then mechanically deformed to a strain between $\epsilon_1$–$\epsilon_2$ to give rise to a martensite with large mechanical strength. The increase in austenitic transformation temperature to above $T_B$ ensures no spontaneous temperature-induced configuration recovery. The original configuration may be recovered, e.g. for the purpose of removal or repositioning, by heating the SMA portion, e.g. by means of warm saline, by passing electric current, by a focused ultrasound radiation, and generally by any physiologically compatible heating method. The austenitic transformation may also be in a direction which is the same as that of the mechanical deformation. This feature may be used for reinforcement of the device after the mechanical isothermal deformation, for increasing the device's strength and fatigue resistance and for reducing recoil.

An embodiment of the invention makes use of the combined mechanical properties of an SMA and of another material having plastic or elastic mechanical properties. Their combination, in accordance with the invention, results in an element with simulated plastic deformation properties, when deformed from an initial to an operational configuration; and under certain conditions, this element can deform back towards the initial configuration in a simulated elastic deformation.

The combination of an SMA and a plastic or elastic component to form a composite element having such properties can be in a variety of ways. For example, the SMA may be coated by the plastic or elastic component. Additionally, plastic or elastic restraining members may be fitted to an SMA in a manner that they will undergo joint deformation. A particular example is the case of a stent which is to be deployed by deformation from a contracted, initial state, to an expanded operational state. Such a stent may be made with the SMA coated by a plastic layer or may be made as an SMA spiral combined with one or more restraining members, e.g. several plastic bands fitted over the stent, a plastic sleeve accommodating the stent within it, etc.

Figure 3:
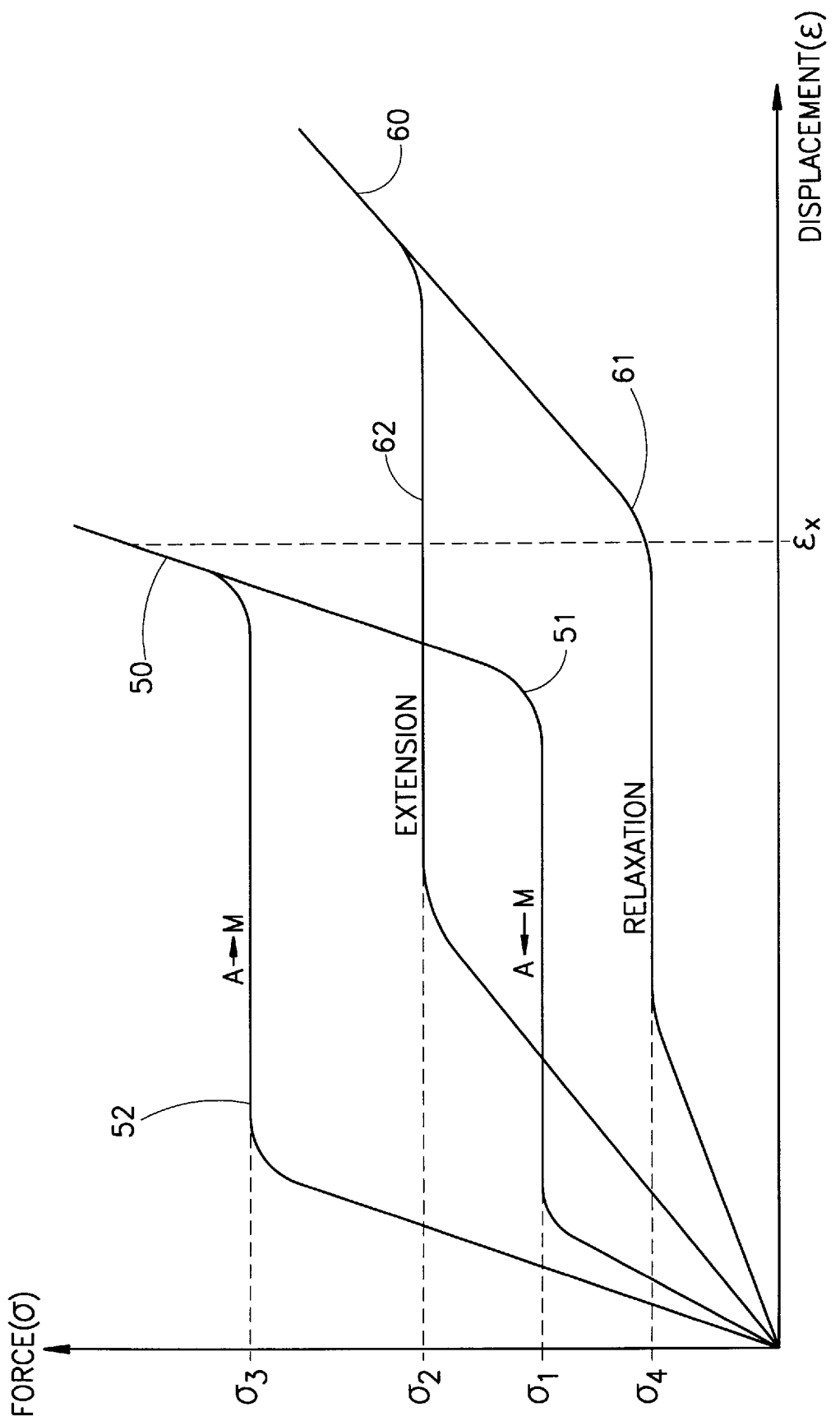
FIG. 3 shows a stress-strain curve for an SMA superelastic (SE) component, and for a second component with different mechanical properties, which are combined together to yield a device displaying simulated plastic deformation properties.

The properties of such composite elements can best be understood with reference to FIG. 3. In FIG. 3, a curve 50, showing the stress-strain relationships of an SMA in its deformation from an austenitic state (lower left hand corner) to the martensitic state (upper right hand corner). Curve 50 has a lower segment 51 which shows the strain-stress relationships in a deformation between martensite and austenite (M–A) and the upper segment 52 shows the strain-stress relationships in the deformation between austenite to martensite (A–M).

Also seen in FIG. 3, is curve 60 displaying the mechanical properties of a second component, e.g. made of a plastic. Similarly as curve 50, curve 60 has also two segments, consisting of a lower segment showing the strain-stress relationships during relaxation, and an upper curve 62 showing a strain-stress relationship during extension.

The SMA in the composite element is initially in a strain-or-stress-induced martensitic state with a total deformation up to $\epsilon_x$. In this state, the SMA is restrained by the second component since its deformation from martensite to austenite exerts a stress $\sigma_1$ while the resistance towards extension of the plastic element is $\sigma_2$. When deformation is forced, e.g. in the case of a stent from a contracted state to an extended state by the use of a balloon catheter, force which has to be applied has to be larger than the difference between $\sigma_2$ and $\sigma_1$.

While the deformation from the initial state to the operational state, which is an M–A deformation, precedes along the lower curve 51, the opposite deformation, A–M deformation, precedes along the upper curve 52; thus the SMA portion displays a resistance to deformation in the opposite direction (namely from the operational state to the initial state), at a force $\sigma_3$. This will the be mechanical resistance force of the SMA against deformation in this opposite direction. The mechanical deformation stress in this opposite direction is a combination of that applied by the second component $\sigma_4$ and that provided by the surrounding tissue. $\sigma_3$ is larger than these combined forces and accordingly the SMA portion will resist this opposite deformation.

Given all the above, it is clear that the composite element will display almost ideal plastic properties in its deformation from the initial to the operational configuration, with practically no recoil once reaching the operational configuration. Furthermore, it is clear that this element has a high mechanical strength against reactive forces which may be exerted by the surrounding tissue organ, namely its collapse.

It is possible to construct the SMA portion such that it will also have an R phase, with a $T_R$ temperature below body temperature. In accordance with this embodiment, the SMA device may be cooled to $T_R$ whereupon it transforms to the R phase. In this phase, it has very low shift modulus and accordingly its resistance to transformation in the opposite direction becomes very low (below $\sigma_4$), and thus the force which will be applied by the second component will cause its deformation from the operational configuration to the initial configuration.

The second component, whose stress-strain relationship is shown in FIG. 3, has some elasticity and some recoil, seeing that $\sigma_4$ is different than the zero. It is obviously also possible to have this component entirely plastic ($\sigma_4=0$); or alternatively, it is possible that this component be elastic, ($\sigma 4$ will be about the same as $\sigma_2$) whereby extension and relaxation will proceed long the same curve. The former component is a plastic component with a very low recoil, and the latter is an elastic component with very high recoil.

In the case of the second component being plastic ($\sigma_4=$ about 0), the composite element provides a wide spectrum of adjustable pressure on the surrounding tissue. Where the second component is elastic, as pointed out above, cooling the temperature below $T_R$, will cause a mechanical deformation towards the initial configuration.

It is possible also to use a plastic element which changes its mechanical properties after loading:$\sigma_2$ after one loading will be less than before loading. Such a composite element will have similar properties to those discussed with reference to FIG. 3.

Some examples of medical devices in accordance with the invention will now be described.

Figures 4, 5:
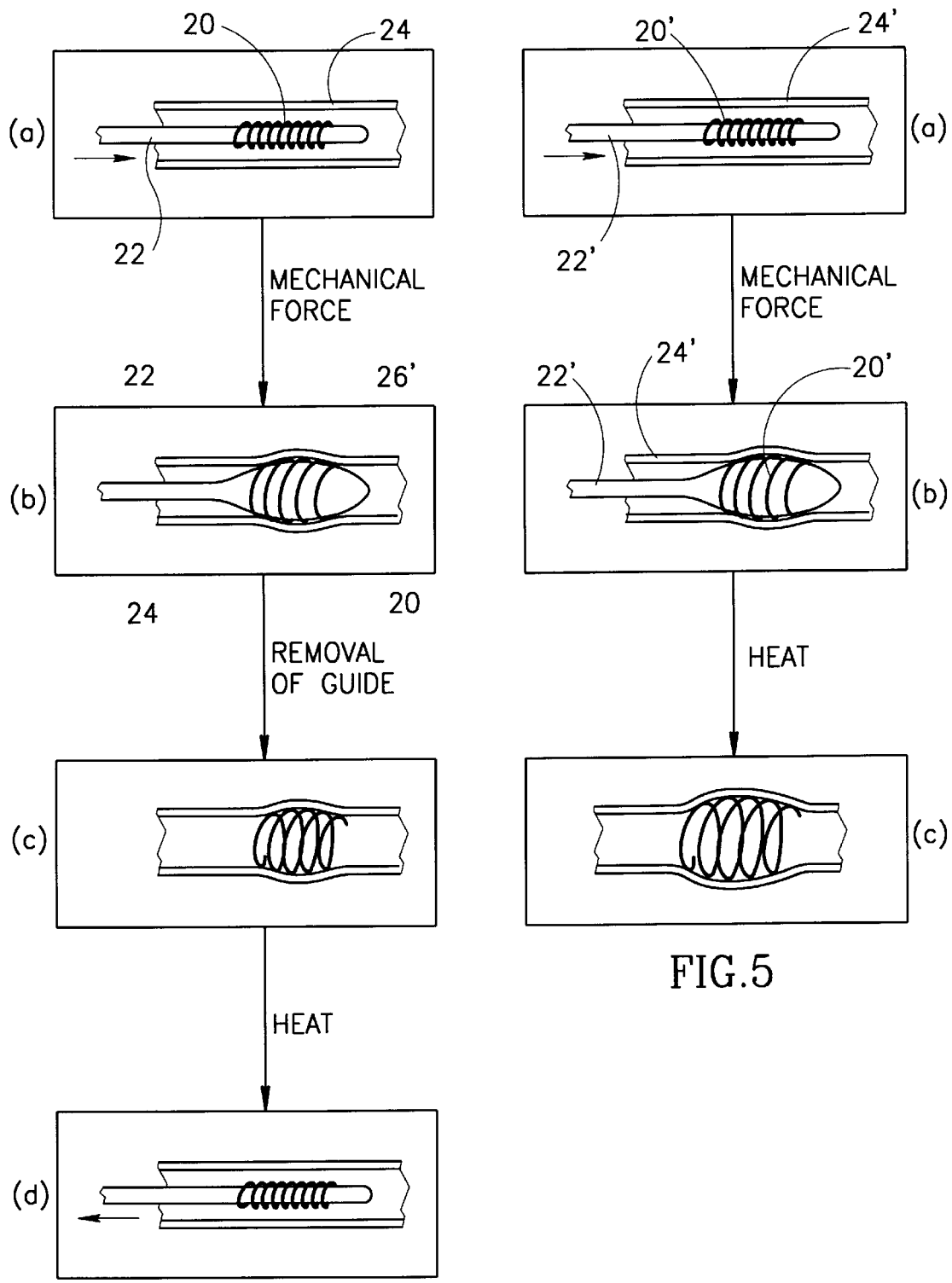
FIG. 4 illustrates an embodiment of a stent of the invention and its deployment in a tubular organ. In this embodiment, the stent has an austenitic configuration, such that the deformation from the martensitic to the austenitic state goes in a direction opposite to the mechanical deformation during deployment.
FIG. 5 shows a stent in accordance with another embodiment of the invention, and its deployment in a tubular organ. In this case, the stent can undergo an austenitic transformation, which results in a configuration change which is in the same direction to that of the mechanical deformation during deployment.

Reference is first being made to FIG. 4, showing a stent 20 held on an end of a balloon catheter 22. In the first step (a), stent 20 is brought into the deployment position, within the tubular organ 24, e.g. an artery, while in an initial position with a relatively low diameter, in which it is held on catheter 22. Once in position: (Step (b)) stent 20 is expanded by a balloon 26 of catheter 22, whereby the diameter of stent 20 increases to its deployment configuration. This mechanical deformation is performed in martensite, with a deformation strain not exceeding $\epsilon_2$ while having high mechanical strength and being fatigue resistant. The stent 22 can then be removed (Step (c)), and the stent will thus become deployed supporting the walls of the tubular organ.

The stent of this embodiment is designed so that it can undergo an austenitic transformation with a deformation which is in a direction opposite to that of the mechanical deformation. In this case, the heating of the stent to a temperature above $A_s'$ (Step (d)), e.g. by means of a warm saline, will cause the stent to shrink to its austenitic configuration, in which it can be removed or redeployed.

Another embodiment of this stent can be seen in FIG. 5. This embodiment, like elements to those of FIG. 4, has been given the same reference involved with a "'" indication.

Steps (a) and (b) are essentially similar to steps (a) and (b) of FIG. 4. In this case, the stent 20' has been made such that the austenitic transformation causes a change in the configuration which goes in the same direction as the mechanical deformation. Thus, by heating the temperature above $A_s'$ (Step (c)), the stent increases in diameter and thereby exerts a stronger force on the surrounding tissue, as a result of the super elastic properties in the austenitic state.

Figure 6:
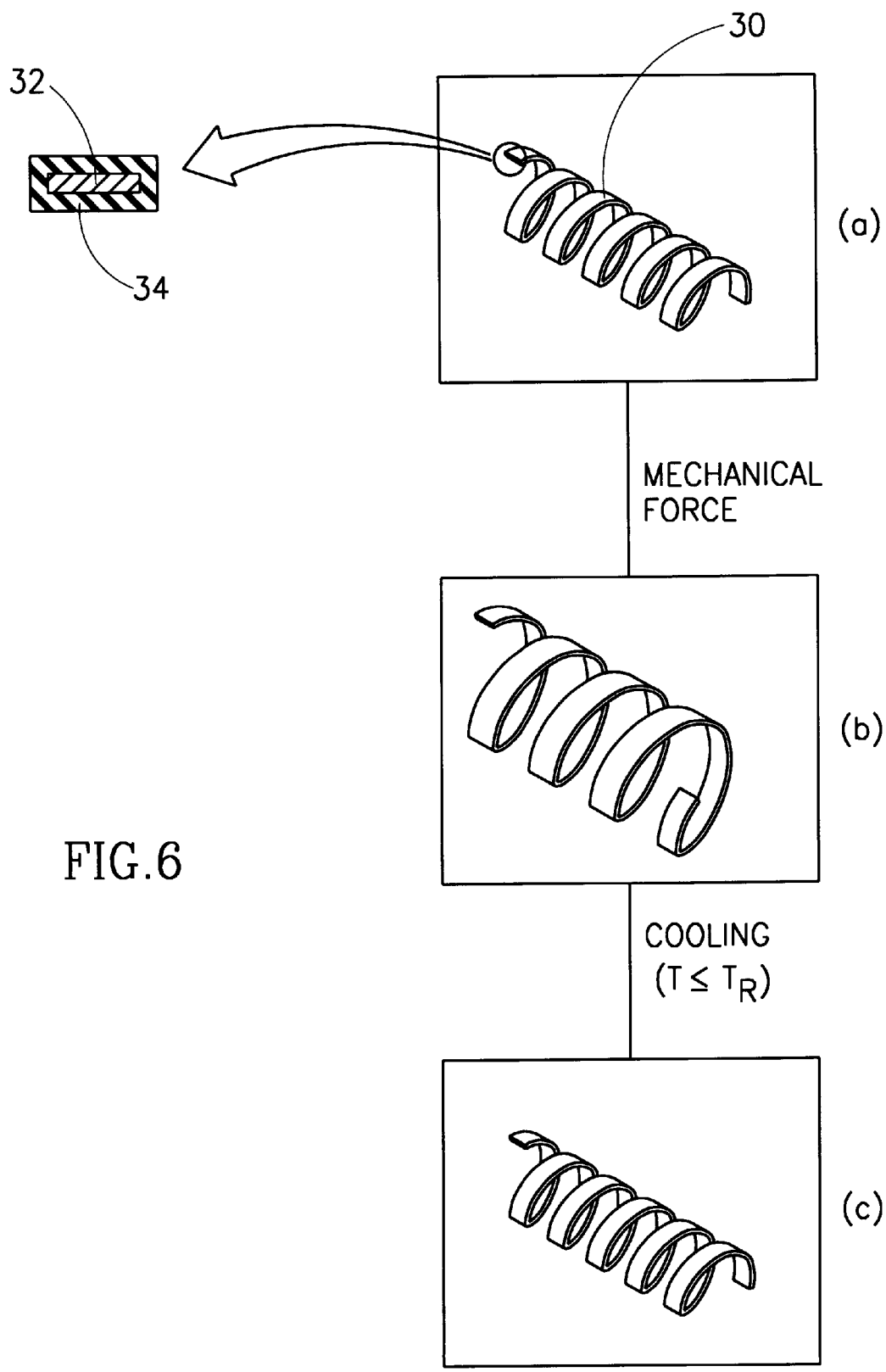
FIG. 6 shows a stent in accordance with another embodiment, which is a composite element made of an SMA component, and another component having plastic or elastic deformation properties.

FIG. 6 shows a stent 30, in accordance with another embodiment, which as can be seen in the cross section of the view on the left, is a composite material comprising an SMA 32, coated by another component 34, which may be a substance with plastic (low recoil) properties, elastic (high recoil) properties, or intermediate properties between the two. By applying a mechanical force, e.g. by a balloon, as in FIGS. 4 or 5, the stent 30 expands from an initial configuration (a) to an operational configuration (b). This mechanical deformation is in fact, a "simulated plastic deformation" as explained above. By cooling to a temperature below $T_R$ (c), the component 34 acts to shrink the stent toward its initial state of (c). It should be noted that rather than coating a second component in the manner described above, the association of the second component to the SMA may be by a variety of other means, e.g. containing an SMA stent within a sleeve made of a plastic substance, by adding one or more restraining members, etc.

The substance from which the second component is made, may typically be a plastic polymeric material, e.g. cardiological polyurethane. However it may also be made from other substances, e.g. metal, rubber, etc.

The stent in the embodiment shown in FIGS. 4–6, may have, for example, an initial diameter of 1.5–2.5 mm., and then may be expanded mechanically to a diameter of about 3.5–4.5 mm. The deformation between a diameter of 2 mm. to a diameter of 3.5 mm. induces a strain of about 2%. The deformation from 1.5 mm. to 4 mm. induces a strain of about 8%.

Figure 7:
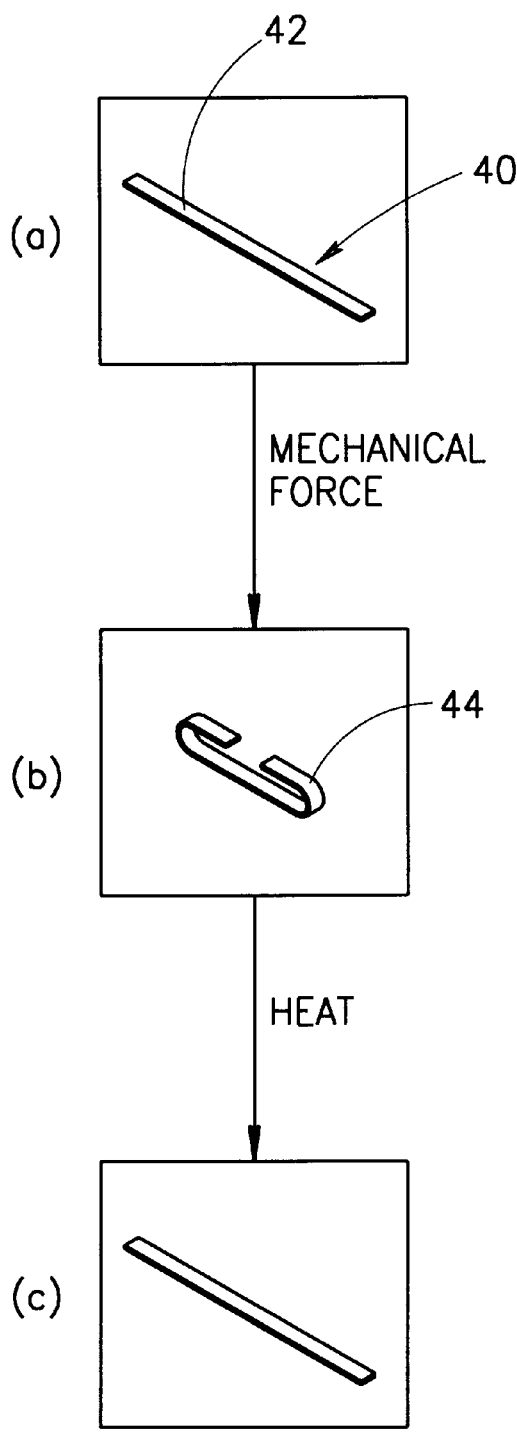
FIG. 7 shows a removable surgical staple, in accordance with an embodiment of the invention, where the austenitic transformation yields a deformation which is in a direction opposite to that of the mechanical deformation during deployment.

FIG. 7 shows a surgical staple 40, which has an initial straight shaped configuration 42(a), and is then deformed mechanically in martensite, into a deployment configuration 44(b). The staple, which is made of an SMA, has an austenitic configuration such that the austenitic transformation yields a deformation which goes in the direction opposite to the mechanical deformation. Thus, by heating, the staple opens to its initial configuration, and can then be removed (c).

Figure 8:
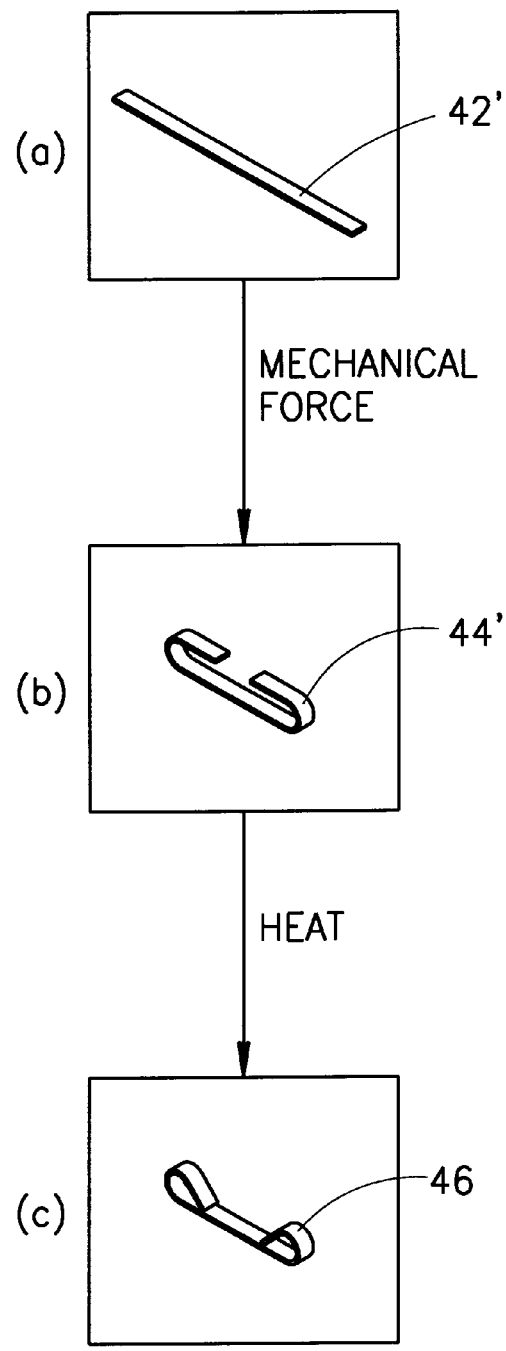
FIG. 8 shows a surgical staple in accordance with another embodiment of the invention, where the austenitic transformation yields a deformation which goes in the same direction as the mechanical deformation during deployment.

In FIG. 8, a similar surgical staple is shown, and accordingly like elements have been given like numbers with a prime indication. In this case, the austentic transformation induces a deformation which goes in the same direction to that of the mechanical deformation, and accordingly, by heating a surgical staple with a higher strain deformation 46, is obtained (c). This serves to further strengthen the tissue binding properties of the staple.

Figure 9:
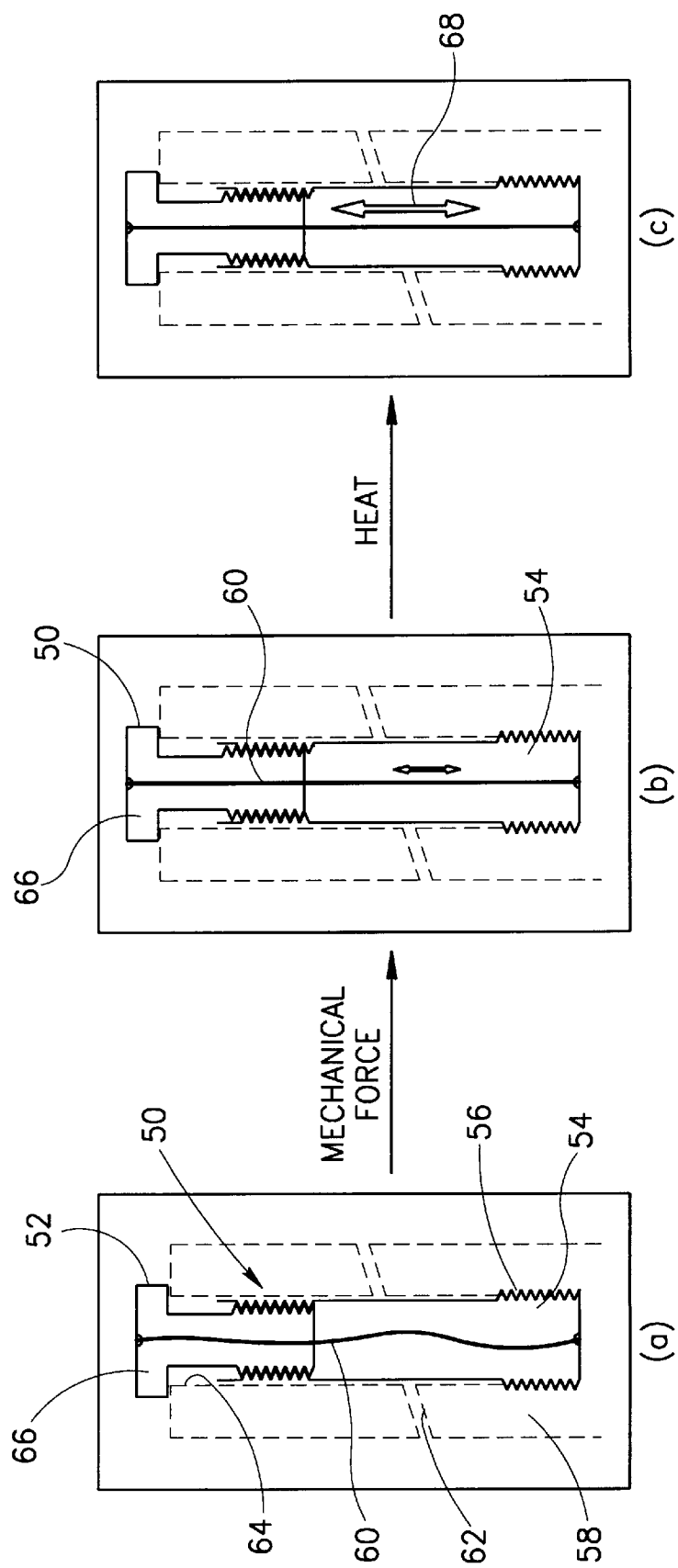
FIG. 9 shows a bone fracture healing device, in accordance with the invention and its deployment to fix a bone fracture.

FIG. 9 shows a bone fixation device (50), which comprises two members 52 and 54, which are screw fitted with one another, with member 54 having an external screw thread at its end 56, for a tight screw engagement with the surrounding bone tissue 58. The device further comprises a tensioning cable 60, made of SMA. In order to fix a fracture 62, in the bone, a bore 64, is drilled in the bone, and the device is inserted until the end 56 is tightly screwed into the bone tissue at the end of the bore, and the head 66 of member 52, rests on the bone's exterior surface. During its screw fitting into the bone tissue, members 52 and 54 move slightly apart from one another and consequently, tensioning cable 60 becomes tensioned from its initial loose state (a) to a tensioned state (b). In one embodiment, the austenitic transformation gives rise to a deformation which is in the opposite direction to the mechanical deformation, and consequently, upon heating a temperature above $A_s'$ (c), cable 60 transforms to austenite and thus forces the two members 52 and 54 together even further (represented by the relatively large arrow 68) thereby pressing the two fractured bone pieces tightly one towards the other.

Figure 10:
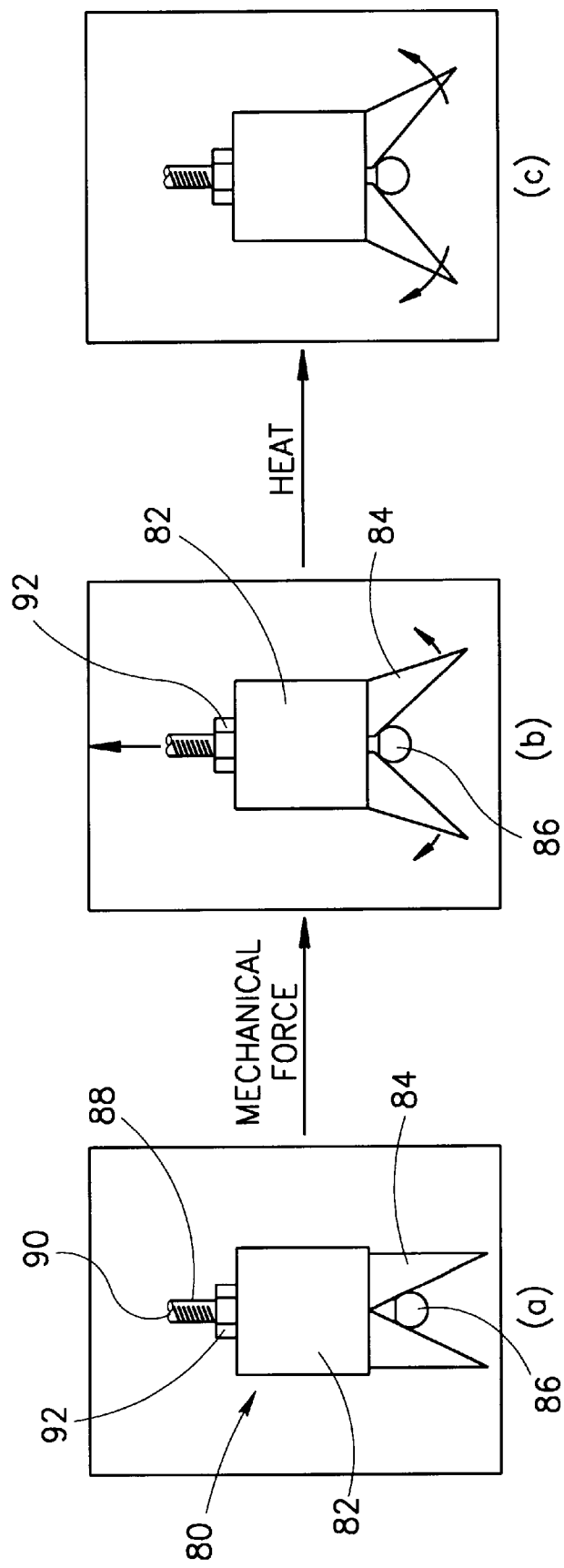
FIG. 10 shows a bone anchor device, where the SMA portion can undergo an austenitic transformation to increase the anchoring force.

FIG. 10 shows a bone anchoring device. The device generally designated 80, has a crown 82, and anchoring legs 84, made of an SMA. The device further has a tensioning arrangement comprising a sphere 86, which is at the end of a rod 88, which is externally screw-threaded at its end 90, and a bolt 92 screw-coupled to end 90. A mechanical tensioning force can be applied by turning bolt 92, pulling sphere 86 from its initial position (a) to a deployed position (b), with this yielding expansion of legs 84. The SMA has an austenitic configuration, such that that the deformation in the austentic transformation is in the same direction to that of the mechanical deformation; accordingly, after heating to a temperature above $A_s$ (c) legs 84, expand even further and provide, by virtue of their super-elasticity, a constant force on the surrounding bone tissue.

Figure 11:
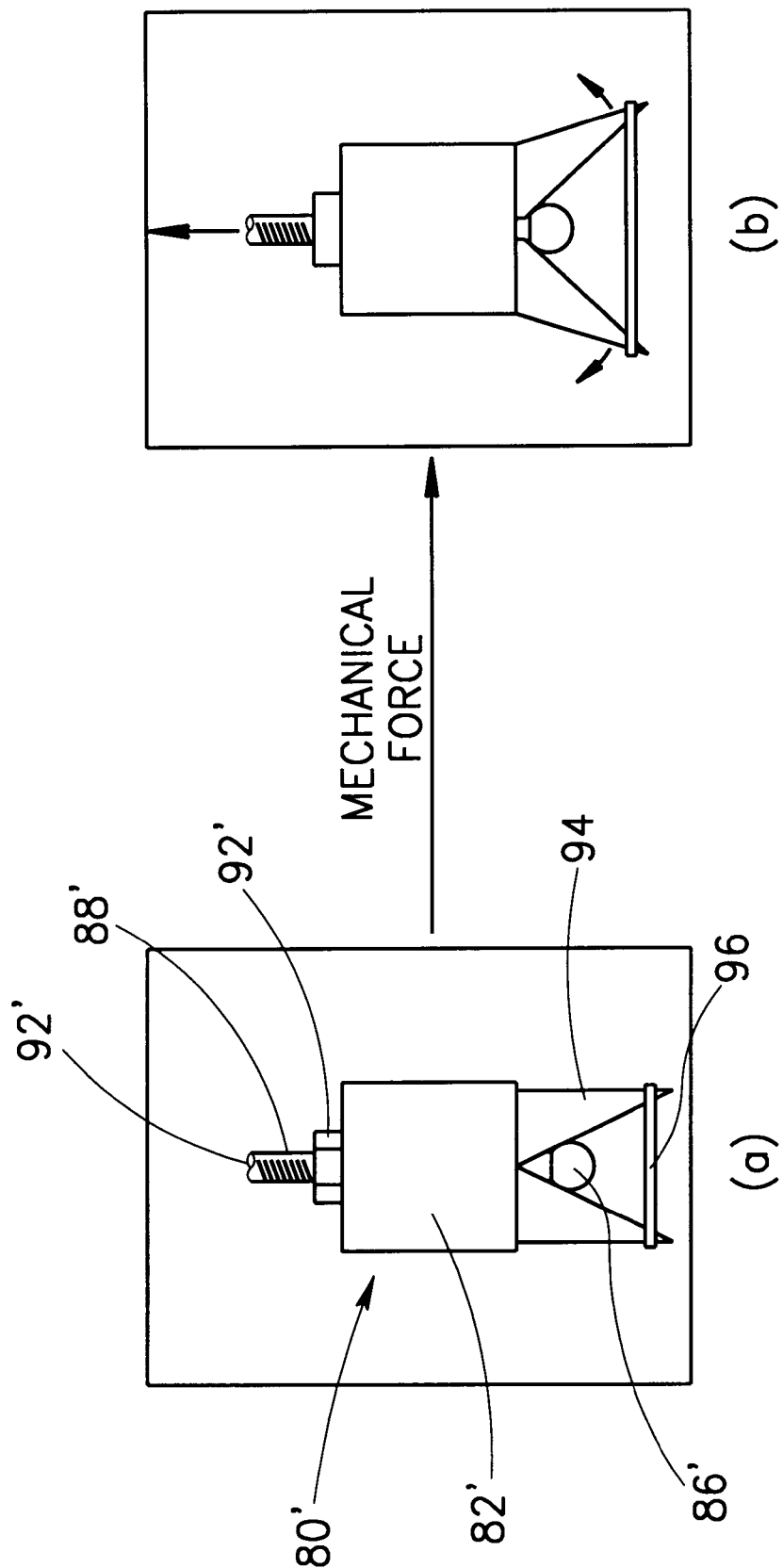
FIG. 11 shows a bone anchoring device, comprising a second component.

A bone anchoring device according to another embodiment of the invention is shown in FIG. 11. Similar elements to those of FIG. 10 have been given the same reference numeral as in FIG. 10 within the prime indication. In this case, anchoring legs 94 are in an MIMS, and are maintained in that state, by the restraining force of plastic band 96. By the application of mechanical force, legs 94, epand, transforming into austenite against the mechanical force of band 96; the overall effect is that of a simulated plastic deformation ensuring that the mechanical deformation will be a simulated plastic deformation.

We claim:

1. A medical device for deployment in a body of an individual, comprising a shape memory alloy (SMA) portion having an austenitic and a martensitic state, with an austenitic memorized configuration and a martensitic memorized configuration at these states, respectively, and being transformable between the martensitic state to the austenitic state by an austenitic transformation occurring at an austenitic transformation temperature, and from the austenitic state to the martensitic state by a martensitic transformation occurring at a martensitic transformation temperature, said SMA portion being capable of acquiring at least two working configurations stable at Physiological body temperature $T_B$, said two working configurations being an initial configuration and an operational configuration to be assumed by it when deployed within the body by mechanical deformation of its initial configuration, said initial configuration is either a memorized austenitic configuration or a martensitic configuration assumed by the SMA portion by a mechanical deformation; the SMA portion in said operational configuration is either in a martensitic state and having a memorized austenitic configuration to which it transforms when heated to a temperature, equal or above the austenitic transformation temperature, which is above said body temperature, or is in an austenitic state, to which it transformed during the mechanical deformation, said memorized martensitic configuration being essentially close to the operational configuration of said SMA portion.

2. A medical device according to claim 1, wherein the SMA portion has in its martensitic operational configuration, an $A_f'$, a finish temperature of the austenitic transformation in said operational configuration, which is higher than the physiological body temperature, $T_B$, and an $M_s$, being a start temperature of the martensitic transformation, which is lower than $T_B$; the SMA portion being deformable, while retaining its martensitic state into said operational configuration; upon heating of the SMA portion to a temperature above $A_f'$, it undergoes an austenitic transformation into the austenitic configuration, which is a different configuration than said operational configuration, being an additional stable working configuration, and remains in the austenitic configuration after the temperature of the SMA returns to $T_B$.

3. A medical device according to claim 2, wherein the transformation from the operational martensitic configuration to the austenitic configuration, when heating the device to a temperature above $A_f'$, is the transformation to an additional working configuration going in the direction opposite to that of said mechanical deformation; said additional working configuration being a removal configuration.

4. A medical device according to claim 2, wherein the austenitic configuration is such that the transformation from the operational configuration to the austenitic configuration, upon heating of the device to a temperature above $A_f'$, goes in a same direction to that of said mechanical deformation, thereby acquiring the additional working configuration being high strength and stiff.

5. A device according to claim 2, having an intermediate state R, between the martensitic and the austenitic states, and having a transformation temperature from the austenitic state to the R state $T_R$, which is higher than $M_s$ and being close to $T_B$, such that at body temperature, the SMA portion is entirely or partially in the R state.

6. A medical device according to claim 2, wherein the deformation of the SMA from the initial shape to the deployment shape is with a strain within a range of $\epsilon_1-\epsilon_2$, with $\epsilon_1$ being a strain level at an end of a horizontal plateau of a stress-strain curve of the SMA, and $\epsilon_2$ is an upper limit of deformation recoverable by a shape memory effect.

7. A medical device according to claim 2, wherein the forced deformation of the SMA portion causes an increase in the austenitic transformation temperature from initial start and finish transformation temperatures of the austenitic transformations, $A_s'$, and $A_f'$, respectively, which are below $T_B$, to austenitic start and finish transformations in the operational configuration, $A_s'$, and $A_f'$, respectively, higher than $T_B$.

8. A device according to claim 7, having an R phase with a $T_R$ close to $T_B$ and is mechanically deformable such that at least one segment of the SMA portion remains in the R phase and at least one other segment is deformed with a strain at a range of $\epsilon_1-\epsilon_2$.

9. A device according to claim 1, comprising:
a first component and a second component associated with one another, such that a deforming mechanical force cause both to deform together; the first component comprising an SMA having an initial configuration in which the SMA is in a mechanically induced martensitic state (MIMS) resulting from a strain-induced or stress-induced martensitic transformation; the second component having mechanical properties such that it resists deformation at a stress, $\sigma_2$, which is larger than stress generated by the SMA when released from said MIMS to the austenitic stress, $\sigma_1$, thereby restraining said SMA in said initial state; the SMA together with the plastic element are mechanically deformable from said initial configuration to an operational configuration, this deformation causing the SMA to transform from said MIMS to the austenitic state; the plastic element yielding a reactive stress, $\sigma_2$, which is less than the resistive stress, $\sigma_3$ of the deformation of the SMA from the operational configuration to said initial configuration, whereby the device is retained in said operational configuration.

10. A device according to claim 9, wherein said second component has a low recoil.

11. A device according to claim 9, wherein the second component has a high recoil, and the SMA has an R phase with a $T_R$ transformation temperature below $T_B$, whereby upon cooling of the SMA to $T_R$ or below, there is a sharp drop of the SMA's elastic modulus giving rise to a decrease in stiffness of the SMA such that said second component can then deform the SMA portion up to at least said initial configuration.

12. A device according to claim 1 being a member of the group consisting of a stent, surgical staple, bone anchor device and bone fraction fixation device.

* * * * *